United States Patent
Guirguis et al.

(10) Patent No.: US 6,354,137 B1
(45) Date of Patent: Mar. 12, 2002

(54) INERTIAL CONFINEMENT CYLINDER FOR EXPLOSIVE CHARACTERIZATION

(75) Inventors: Raafat H. Guirguis, Fairfax, VA (US); Harold W. Sandusky, Laurel; George P. Chambers, La Plata, both of MD (US)

(73) Assignee: The United States of America as Represented by the Secretary of the Navy, Washington, DC (US)

(*) Notice: Subject to any disclaimer, the term of this patent is extended or adjusted under 35 U.S.C. 154(b) by 0 days.

(21) Appl. No.: 09/783,282

(22) Filed: Feb. 9, 2001

(51) Int. Cl.[7] .......................... G01N 33/22; F42B 33/00
(52) U.S. Cl. ........................ 73/35.17; 73/35.14; 86/50
(58) Field of Search .............................. 73/35.14, 35.15, 73/35.16, 35.17; 86/50

(56) References Cited

U.S. PATENT DOCUMENTS

| | | | | |
|---|---|---|---|---|
| 253,914 A | * | 2/1882 | Dean ......................... 73/35.14 |
| 1,049,187 A | * | 12/1912 | Wilson ....................... 73/35.14 |
| 1,068,904 A | | 7/1913 | Ionides, Jr. |
| 1,523,290 A | * | 1/1925 | Rimailo ....................... 73/35.14 |
| 1,801,449 A | * | 4/1931 | Olsen et al. ................ 73/35.14 |
| 2,335,779 A | | 1/1943 | Mazzei .......................... 102/7 |
| 2,483,803 A | * | 10/1949 | Bridgman ............... 73/35.17 X |
| 2,673,660 A | | 3/1954 | Nordin ......................... 220/85 |
| 2,812,655 A | * | 11/1957 | Curran ........................ 73/35.14 |
| 2,937,530 A | * | 5/1960 | Haley ......................... 73/865.6 |
| 2,972,247 A | * | 2/1961 | Zablocki ..................... 73/35.14 |
| 3,268,107 A | | 8/1966 | Sperling ....................... 220/63 |
| 3,367,490 A | | 2/1968 | Jensen et al. .................. 206/65 |
| 3,434,336 A | | 3/1969 | Harr ............................... 73/35 |
| 3,554,008 A | * | 1/1971 | Zaid et al. .................. 73/35.16 |
| 3,670,559 A | * | 6/1972 | Bement ....................... 73/35.15 |
| 3,820,435 A | | 6/1974 | Rogers et al. ................. 89/1 R |
| 4,015,526 A | * | 4/1977 | Bond et al. .................. 181/116 |
| 4,110,136 A | | 8/1978 | Hershkowitz et al. ......... 149/47 |
| 4,174,624 A | | 11/1979 | Shrum ........................... 72/56 |
| 4,300,962 A | | 11/1981 | Stinecipher et al. .......... 149/47 |
| 4,474,052 A | * | 10/1984 | Bodurtha, Jr. et al. ..... 73/35.17 |
| 4,478,126 A | * | 10/1984 | Holmlund et al. ............. 86/50 |
| 4,621,559 A | * | 11/1986 | Ohlson ........................... 86/50 |
| 4,632,041 A | * | 12/1986 | Ohlson ....................... 109/1 S |
| H000314 H | * | 8/1987 | Betts ........................... 206/523 |
| 4,845,995 A | * | 7/1989 | Kaste et al. .................. 73/794 |
| 4,932,239 A | | 6/1990 | Regallbuto ..................... 73/35 |
| 4,990,312 A | * | 2/1991 | Rucker et al. ................ 422/78 |
| 5,046,567 A | * | 9/1991 | Aitken et al. ................ 175/4.6 |
| 5,348,178 A | * | 9/1994 | McLain ..................... 220/88.1 |
| 5,613,453 A | | 3/1997 | Donovan ..................... 110/237 |
| 5,833,782 A | | 11/1998 | Crane et al. .................. 156/60 |
| 5,884,569 A | * | 3/1999 | Donovan ..................... 110/346 |

OTHER PUBLICATIONS

A Closed Water–Filled Cylinder Test for Characterizing Non–Ideal Explosives, R. Guirguis, et al., Naval Surface Warfare Center, Indian Head, MD 20640, 97 APS Paper.

A Closed Water–Filled Cylinder to Characterize Non–Ideal Explosives, R. Guirguis, et al., Naval Surface Warfare Center, Indian Head, MD 20640, 11th Det. Symposium.

A Closed Water–Filled Cylinder Test for Characterizing Non–Ideal Explosives, R. Guirguis, et al., Naval Surface Warfare Center, Indian Head, MD 20640, 97 JANNAF PSHS.

* cited by examiner

*Primary Examiner*—Daniel S. Larkin
*Assistant Examiner*—Jay L. Politzer
(74) *Attorney, Agent, or Firm*—Mark Homer

(57) ABSTRACT

A reusable small-scale explosive testing apparatus has a structural member with a curved internal chamber, a head piece that inserts into the chamber, a cap to hold the head piece, a pressure-time gage, water to fill the chamber and a pressure release mechanism. The apparatus is used to test small amounts of explosive.

20 Claims, 2 Drawing Sheets

INERTIAL CONFINEMENT CYLINDER FOR EXPLOSIVE CHARACTERIZATION

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

BACKGROUND OF THE INVENTION

1. Field of the Invention

The present invention relates to a small scale explosive testing apparatus and method. More particularly, the small scale explosive testing apparatus of the present invention is reusable.

2. Brief Description of the Related Art

Non-ideal underwater explosives usually contain a significant portion of slow reacting components—for example, a mixture of aluminum and ammonium perchlorate particles. Only a fraction of the explosive's energy is released early enough to contribute to sustaining the detonation front which, therefore, propagates at lower velocity and pressure than in ideal explosives. The slow-reacting components release the remaining energy late, after the Chapman-Jouguet (CJ) surface, often even after the bubble has expanded several times the volume of the charge.

The slow release of energy poses a challenge for conventional testing methods. The detonation products have to remain longer at high temperature and pressure in order to allow the non-ideal components enough time to react. This is accomplished by either using a large explosive charge or by confining the detonation products. In underwater tests, the inertial resistance of the water helps slow the expansion of the products, but because the bubble expands in all directions, the resulting spherical divergence quickly reduces the pressure and temperature inside.

Typical underwater explosives are non-ideal and therefore characterized by their late-time energy release. In order for late-time reactions to occur, the reaction products have to be maintained together under high pressure for periods on the order of several milliseconds. Small-Scale tests such as the Moby-Dick test can observe late-time reactions, but cannot reach high pressures, such as approximately 1 kbar, which are required to evaluate the rates and pressure dependencies of the late-time reactions. In the Moby-Dick test, the bubble expansion is restricted to one-direction only in order to reduce the divergency and slow the rate of pressure decay.

Large scale explosive evaluation shots, typically between 50 and 100 kg, are carried out underwater in quarries to evaluate this late-time performance under high pressure since the product gases are held together due to the inertial confinement of the water. However, these large scale shots are expensive and difficult to instrument.

Explosive and pressure containment systems have been disclosed in several patents. U.S. Pat. No. 1,068,904 to Ionides, Jr. discloses a means for preventing the backward propagation of a flame along a conduit. U.S. Pat. No. 2,335,779 to Mazzei discloses a casing for carriers for nitro-glycerin which may be filled with water. U.S. Pat. No. 2,673,660 to Nordin discloses a pressure relief device having a tubular body. U.S. Pat. No. 3,268,107 to Sperling discloses a container for hazardous material having cylindrical sidewalls and a domed or partially spherical top surface. U.S. Pat. No. 3,367,490 to Jensen, et al. discloses a container for free flowing materials. U.S. Pat. No. 3,434,336 to Harr discloses an explosion barrier having foam to prevent an explosion from spreading between two chambers. U.S. Pat. No. 3,820,435 to Rogers, et al. discloses a spherical walled containment vessel with a plurality of access ports that is evacuated to a pressure of about 500 microns. U.S. Pat. No. 4,174,624 to Shrun, U.S. Pat. No. 5,833,782 to Crane, et al., and U.S. Pat. Nos. 5,613,453 and 5,884,569 to Donovan disclose apparatuses for explosion containment.

Explosive testing devices also have been disclosed in several patents. U.S. Pat. No. 4,300,962 to Stinecipher, et al. discloses an aquarium test defined by detonating a cylindrical charge in a plexiglass aquarium filled with water. U.S. Pat. No. 4,110,136 to Hershkowitz, et al. discloses a tube for a confined small-scale detonation velocity and dent test with a steel cylinder. U.S. Pat. No. 4,932,239 to Regalbuto discloses a testing apparatus employed to test explosive charges.

Drafted documents entitled "A Closed Water-Filled Cylinder Test for Characterizing Non-Ideal Explosives" by R. Guirguis, et al., Naval Surface Warfare Center, Indian Head, Md., 97 APS Paper; "A Closed Water-Filled Cylinder to Characterize Non-Ideal Explosives" R. Guirguis, et al., Naval Surface Warfare Center, Indian Head, Md., $11^{th}$ Det. Symposium; and "A Closed Water-Filled Cylinder Test for Characterizing Non-Ideal Explosives" by R. Guirguis, et al., Naval Surface Warfare Center, Indian Head, Md., 97 JAN-NAF PSHS, the disclosures of which are herein incorporated by reference, describe several aspects of small-scale explosive testing.

Although in the above identified patents and references several explosive containment or testing devices are disclosed, none of the patents discloses a reusable small scale testing apparatus for non-ideal explosives. The present invention addresses this and other needs.

SUMMARY OF THE INVENTION

The present invention includes a reusable small-scale explosive testing apparatus comprising a structural member having a closed end and a receiving end forming a hollow cylindrical chamber therein, the chamber having a curved radius internal surface at the closed end and the chamber extending through the structural member at the receiving end, the chamber further having a substantially constant radius along the length of the structural member, the receiving end having an externally threaded circumference thereon, a head piece having an insertion component and covering component, wherein the insertion component fits into the chamber on the receiving end and partially fills the chamber, the covering component resting adjacent to the receiving end, a cap forming a cavity therein configured to receive the head piece, the cavity further forming internally threaded surface for mating with the externally threaded circumference of the structural member, a gage configured for units of pressure versus time measurements, a confinement liquid component of sufficient volume to fill the chamber for testing and means for releasing pressure extending from the structural member through the head piece and cap, wherein the means for releasing pressure is capable of retaining and releasing high pressures from the structural member.

The present invention also includes a method for small-scale explosive testing, comprising the steps of providing a reusable small-scale explosive testing apparatus comprising a structural member having a closed end and a receiving end forming a hollow cylindrical chamber therein, the chamber having a curved radius internal surface at the closed end and the chamber extending through the structural member at the receiving end, the chamber further having a substantially constant radius along the length of the structural member, the receiving end having an externally threaded circumference thereon, a head piece having an insertion component and covering component, wherein the insertion component fits into the chamber on the receiving end and partially fills the chamber, the covering component resting adjacent to the receiving end, a cap forming a cavity therein configured to receive the head piece, the cavity further forming internally threaded surface for mating with the externally threaded circumference of the structural member, a gage configured for units of pressure versus time measurements, a confinement liquid component of sufficient volume to fill the chamber for testing and means for releasing pressure extending from the structural member through the head piece and cap, wherein the means for releasing pressure is capable of retaining and releasing high pressures from the structural member, inserting a sample amount of explosive into the chamber, filling the chamber with the confinement liquid, fitting the headpiece onto the receiving end of the structural member, screwing the cap onto the structural member, detonating the explosive sample, measuring the resulting high pressure of the detonated explosive sample, and releasing the high pressure from within the chamber.

Additionally, the present invention includes a pressure evaluation product produced by the process comprising the steps of providing a reusable small-scale explosive testing apparatus comprising a structural member having a closed end and a receiving end forming a hollow cylindrical chamber therein, the chamber having a curved radius internal surface at the closed end and the chamber extending through the structural member at the receiving end, the chamber further having a substantially constant radius along the length of the structural member, the receiving end having an externally threaded circumference thereon, a head piece having an insertion component and covering component, wherein the insertion component fits into the chamber on the receiving end and partially fills the chamber, the covering component resting adjacent to the receiving end, a cap forming a cavity therein configured to receive the head piece, the cavity further forming internally threaded surface for mating with the externally threaded circumference of the structural member, a gage configured for units of pressure versus time measurements, a confinement liquid component of sufficient volume to fill the chamber for testing and means for releasing pressure extending from the structural member through the head piece and cap, wherein the means for releasing pressure is capable of retaining and releasing high pressures from the structural member, inserting a sample amount of explosive into the chamber, filling the chamber with the confinement liquid, fitting the headpiece onto the receiving end of the structural member, screwing the cap onto the structural member, detonating the explosive sample, measuring the resulting high pressure of the detonated explosive sample, and releasing the high pressure from within the chamber.

The small-scale tests provide detonation products of an explosive that are confined at high pressure in a closed cylinder completely filled with water. Numerical simulations of the test show that although the dynamic effects of the shock induced into the water reduce the pressure below the theoretical maximum achievable if all processes were quasi-static, the residual equilibrium pressure is still high enough for the slow reactions of non-ideal explosives to proceed at a finite measurable rate.

DETAILED DESCRIPTION OF THE PREFERRED EMBODIMENT

The present invention includes an apparatus, method and product for determining the performance of explosive compositions, particularly, non-ideal and underwater explosives, in a small-scale test. A small scale explosive testing apparatus has a hollow cylindrical chamber, which is filled with a confinement liquid such as water, where a test explosive is placed, sealed and detonated. Leads extending out of the top of the apparatus allow current input into the apparatus to initiate the charge, using a detonator. Super-pressure lines with conforming external valves release the pressure created within the hollow cylindrical chamber after the explosive event therein. A gage, attached in an elbow in the pressure line or in the head of the apparatus, measures the pressure generally as a function of time during detonation of the explosive. This measurement of the created pressure provides data for evaluating the explosive potential of the explosive samples. The present invention may be used repeatedly to obtain a resulting pressure evaluation product of the tested explosive.

Figure 1:
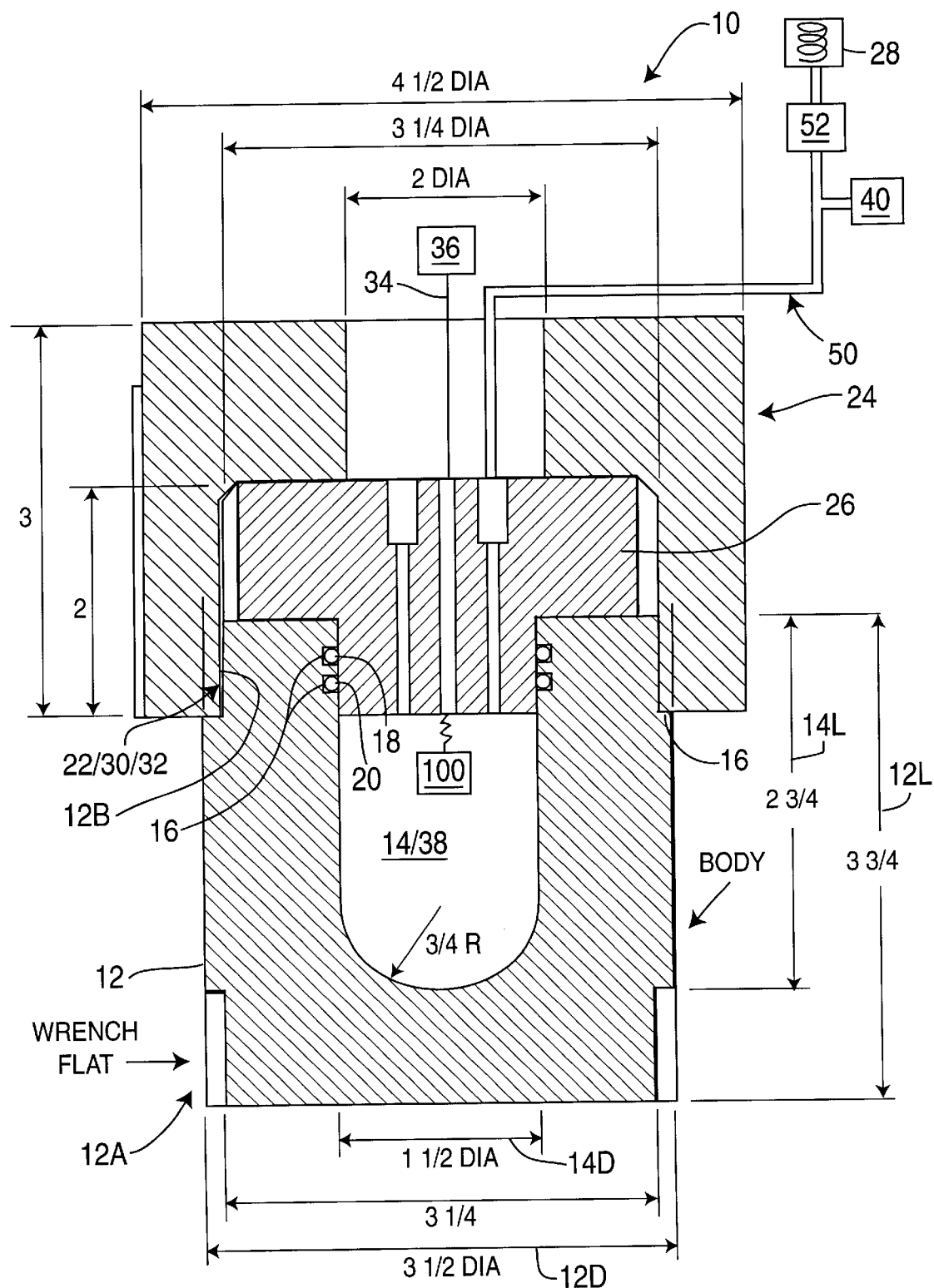
FIG. 1 illustrates a small scale explosive testing apparatus of the present invention; and, FIG. 2 is a pressure-time plot testing explosives using the present invention.

As seen in FIG. 1, a reusable small-scale explosive testing apparatus 10 includes a structural member 12 forming, and substantially enclosing, a hollow cylindrical chamber 14 within the structural member 12. The structural member 12 forms the hollow cylindrical chamber 14 having a closed end. 12A, with the opposite end, referred herein as the receiving end 12B, forming an open conduit between the interior of the hollow cylindrical chamber 14 and the outside of the structural member 12 to permit open communication between the hollow cylindrical chamber 14 and the outside of the structural member 12. The hollow cylindrical chamber 14 extends along the length and through the structural member 12 between the closed end 12A and receiving end 12B. The closed end 12A of the structural member 12 preferably forms a rounded or curved radius (R) on the internal surface of the hollow cylindrical chamber 14. Preferably, the receiving end 12B on the open side of the hollow cylindrical chamber 14 maintains a constant circular diameter throughout its length to the hollow cylindrical chamber 14 and the end of the structural member 12.

The structural member 12 comprises any suitable material that does not significantly deform during an explosive event for small scale testing, with the proper material determinable by those skilled in the art. Preferably, the material comprises a high strength steel, titanium, or combinations thereof. Most preferably, the material comprises high strength steel.

The structural member 12 comprises any suitable dimensions for small scale explosive detonation as determinable by those skilled in the art. Preferably, the length 12L of the structural member 12 ranges from about 3 inches to about 30 inches between the closed end 12A and the receiving end 12B. More preferably, the length 12L of the structural member 12 ranges from about 3 inches to about 20 inches, with the length 12L of the structural member 12 most preferably ranging from about 3 inches to about 12 inches. Preferably, the diameter 12D of the structural member 12 ranges from about 3 inches to about 20 inches, with a more preferably diameter 12D ranging from about 3 inches to about 12 inches. However, larger dimensions, such as fifty

(50) gallon containment areas, may be used. The hollow cylindrical chamber 14 may range, for example, between from about 2 inches to about 20 inches in length 14L, more preferably from about 2 inches to about 10 inches, and from about 1 inch to about 12 inches in diameter 14D, more preferably from about 1 inch to about 6 inches.

The receiving end 12B of the structural member 12 comprises a connecting means 22 for attaching an enclosing structure 28 onto the structural member 12. The connecting means 22 preferably comprises a mechanism that attaches the enclosing structure 28 onto the outside of the structural member 12, such as a screw mechanism or externally threaded circumference 30 formed from the structural member 12, that mates with and cooperatively engages opposing, and internally threaded circumference, threads 32 within the formed cavity of a cap 24. The cap 24 of the apparatus 10 fits over the receiving end 12B of the structural member 12, secured by the internally threaded circumference 32 of the cap 24 cooperatively engaging the externally threaded circumference 30 of the structural member 12 to bind the cap 24 and structural member 12 sufficiently to withstand an explosive event within the hollow cylindrical chamber 14. Preferably the internally 32 and externally 30 threaded circumferences comprise a caliber of from about 4 threads/inch to about 12 threads/inch, more preferably from about 6 threads/inch to about 10 threads/inch, and most preferably approximately 8 threads/inch. The internally 32 and externally 30 threaded circumferences extend a distance sufficient to bind the cap 24 and structural member 12 for the purposes herein. Preferably, the internally 32 and externally 30 threaded circumferences extend a distance of from about 3 inches or less (i.e., from about 12 threads/inch to about 36 threads/inch), and more preferably from about 1.5 inches to about 2 inches.

When the cap 24 is placed on the structural member 12, the cavity area of the cap 24 is located within the confines of the area between the cap 24 and the structural member 12. A head piece 26 is placed within the cavity area of the cap 24 that is configured to resistively fit within the formed cavity area once the cap 24 is secured to the structural member 12. The head piece 26 become resistively fitted between the cap 24 and structural member 12 when there is substantially no movement of the head piece 26 when placed therebetween during the attachment of the cap 24 to the structural member 12. When placed between the cap 24 and structural member 12, the head piece 26 fits into the hollow cylindrical chamber 14 on the receiving end 12A, and when placed in the hollow cylindrical chamber 14 partially fills the hollow cylindrical chamber 14. Once inserted into the hollow cylindrical chamber 14, the head piece 26 is covered with the cap 24, which is screwed onto the structural member 12. With the head piece 26 resistively fixed adjacent to the receiving end 12B, the hollow cylindrical chamber 14 becomes effectively sealed for small-scale explosive detonation. The head piece 26 and cap 24 may comprises any suitable material that does not significantly deform during an explosive event for small scale testing, with the proper material determinable by those skilled in the art. Preferably, the material comprises a high strength steel, titanium, or combinations thereof. More preferably, the material comprises high yield strength steel, particularly when the structural member 12 comprises a like material.

The cap 24 is fitted onto the structural member 12 using a double o-ring seal 16. The double o-ring seal 16 comprises a first 18 and second 20 o-ring, with a preferred spacing between the first 18 and second 20 o-rings comprising a distance of from about ½ inch to about 1 inch. Pressure is allowed to build up between the two o-rings 16 which opposes pressure build up in the hollow cylindrical chamber 14.

Within the structure of the head piece 26, leads 34 extend therethrough, and out of the top of the head piece 26 and cap 24. The detonator leads 34 are sealed into the head piece 26 of the apparatus 10, prior to assembly, using 5-minute epoxy manufactured by ITW Devcon of Danvers, Mass. The leads 34 connect to an electronic switch 36, or other known detonation initiator, for proper detonation of an explosive 100 located within the confines of the hollow cylindrical chamber 14, with the proper selection of the electronic switch 36 determinable by those skilled in the art. A means for releasing pressure, such as super-pressure lines, or pressure release hoses, 50 also extend out of the hollow cylindrical chamber 14, through the head piece 26 and cap 24, to an external valve 52. The super-pressure lines 50 provide a conduit to release accumulated pressure from inside of the hollow cylindrical chamber 14 by opening the external valve 52 after detonation of the explosive 100 has occurred and pressure has been created within the hollow cylindrical chamber 14. Coincident with the super-pressure lines 50 or separately attached, a gage 40 is used to measure and record the detonation data, generally as a function of time, during occurrence of the explosive event. Preferably, a means for releasing pressure 28 is attached to the super-pressure lines 50 to regulate the release of pressure from the structural member 12. More preferably, the means for releasing pressure 28 comprises a capture container connected to the end of the pressure release hoses 28.

The gage 40 may comprise any suitable measuring device for the anticipated pressures of the small scale explosive test, such as a transducer gage, tourmaline gage, ytterbium gage, carbon-resister gage, carbon foil gage or PVDF gage, with an appropriate selection of gage 40 being determinable by those skilled in the art. Preferably, the gage 40 comprises a tourmaline gage. More preferably, there are multiple pressure-time gages use for measurement of the created pressures. The tourmaline gage is mounted in the head piece 26 using an appropriate compound, such as a clear Silicone rubber compound, e.g., RTV615A manufactured by General Electric of Waterford, Mass., which is generally vacuum outgassed to remove trapped air from the compound prior to curing. The silicone rubber remains in contact with the water inside the apparatus 10 during the shot and transfers the pressure loading to the tourmaline gage which is potted inside of the apparatus 10. Preferably, a suitable cable for the gage, such as RG-174 cable, is epoxied into the head piece 26 using an appropriate compound for bonding, such as M-bond Curing Agent, type 15 manufactured by Measurements Group, Inc. of Raleigh, N.C. to prevent the water from leaking from the apparatus 10 during high pressure loading. Proper compound selection for use with the apparatus 10 may be determined by one skilled in the art in light of the disclosure herein.

In operation, small-scale explosive testing occurs with the presently described reusable small-scale explosive testing apparatus 10 with the placement of a sample explosive into the reusable small-scale explosive testing apparatus 10. Prior to detonation, a confinement liquid, such as water, mineral oil or other known fluid to provide inertial confinement, with water preferred, is filled into the hollow cylindrical chamber 14 sufficiently to fill the volume of the hollow cylindrical chamber 14 for detonation of the explosive 100. The hollow cylindrical chamber 14 is effectively sealed with the head piece 26 and cap 24 by fitting the headpiece 26 onto the receiving end 12B of the structural member 12, screwing the cap 24 onto the structural member 12 over the head piece 26, and detonating the explosive sample. With detonation, the gage 40 is used to measure the resulting high pressure of the detonated explosive sample. After detonation, the high pressure is released from the hollow cylindrical chamber 14. Bubblepack may be used to line the walls inside the structural member 12 to provide an air gap and limit prompt internal pressures inside the apparatus 10.

The present invention permits repeated use of the reusable small-scale explosive testing apparatus 10. After detonation, the apparatus 10 may be manually disassembled with the hand removal of the cap 24 from the structural member 12. Testing pressures may range from about 100,000 psig or less, using a sample amount of explosive 100 of from about 10 grams or less, with preferred amounts of explosive 100 ranging from about 1 gram to about 100 milligrams. Pressure testing includes the release of pressure from the structural member 12 using the means for releasing pressure 50 that passes through the head piece 26 and cap 24. The means for releasing pressure 50 is used to retain and release the created high pressures from the structural member 12. The testing of the explosive 100 provides a pressure evaluation product using the method of testing. Several small-scale explosive tests may be conducted using the same apparatus 10. Generally, from about 15 to about 20 explosive tests may be conducted with any particular apparatus 10.

In a preferred embodiment, the small-scale explosive testing apparatus 10 has a water-filled steel cylinder capable of confining a small-scale, i.e., less than 1 gram, detonation that is instrumented with transducer and carbon resistor gages to measure shock and quasistatic pressures. The small-scale explosive testing apparatus 10 is robust and reusable having a structural member 12 which measures approximately 3.75 inches in length 12L, 3.5 inches in diameter 12D, with a cylindrical chamber 2.75 inches in length 14L, 1.5 inches in diameter 14D and 0.75 inches in radius R. Additionally a 32 $\mu$inch surface finish is formed on the head piece 26 for placement of the o-ring.

The small-scale explosive testing apparatus 10 permits performance evaluation of underwater explosives in order to be able to calculate the effect of underwater targets of its munitions, and to characterize the performance of non-ideal explosives 100. This is done using gram and sub-gram quantities of explosives 100, saving considerable time and expense in conducting the testing, as compared to "quarry shots" and other like tests. The small-scale explosive testing apparatus 10 maintains sufficient inertial confinement to fully and accurately characterize underwater explosives. Producing a detonation in an enclosed water-filled cylinder confines reaction products long enough to allow non-ideal reactions to occur. The apparatus 10 characterizes the effectiveness of various additives to ANFO compositions. Typically, results from small-scale tests with this explosive have not reliably scaled-up due to the inability of the small-scale tests to simulate the pressures and confinement encountered in large scale shots. The apparatus 10 allows rapid screening through a variety of candidate additives without having the time and expenses associated with large-scale testing. Additionally, the apparatus 10 can preserve reaction products for subsequent chemical analysis.

By characterizing underwater explosives, the effect on underwater targets and suitability for specific warfare applications may be determined. As the most effective underwater explosives are non-ideal, characterizing these non-ideal explosives becomes important. Experiments using the water-filled closed apparatus 10 may characterize non-ideal explosives, as well as measure EOS parameters directly. High shock pressures are measured in a confined water system, allowing measurement of sustained quasi-static pressures.

The apparatus 10 provides several advantages over traditional testing methods which require large scale tests in quarries. The cost for a small-scale test is often a fraction of that required for a large-scale-test. The reusability and rapid turn around time of the closed bomb tests makes it very cost effective and versatile. Because the test is so small, on the order of 1 gram or less, the test has far less environmental impact than- a large scale, i. e., 100 lb., test required for characterization. Reaction products are typically small quantities of CO and $CO_2$.

Testing Procedures and Measurements

The test presented here is a closed version of the Guirguis Hydro-Bulged Cylinder (GHBC) test in which a small (grams) explosive (PETN) charge was detonated at the center of an open-ended water-filled steel structural member of the present invention. A streak camera recorded the radial expansion of the outer wall, while a LASER interferometer measured its velocity. The deformation of the structural member was used to measure the total energy of the explosive. The pressure at the interface between water and metal was measured using a tourmaline crystal. To characterize non-ideal explosives, the apparatus is closed, confining the detonation products indefinitely at high pressure. A cap and head piece are securely fitted into the structural member, sealed with a double o-ring. The pressure of the explosive event is measured off the axis of the interface between the water and the head piece, with the rigidity of the head piece allowing use of a piezo-electric transducer. The expansion of the apparatus is measured using strain gauges.

The Second Law of Thermodynamics indicates that if all the processes involved are quasi-static, the pressure will monotonically build up to the maximum static pressure that can be contained inside the cylinder. The detonation products are held in a fixed-volume bubble equal to the volume of the explosive charge, until the pressure and all other thermodynamic properties equilibrate. The corresponding final state is the point on the reacted Hugoniot having the same density as the solid explosive. The bubble is allowed to isentropically expand, i.e., slowly, such as to remain uniform, and adiabatically, without any heat loss to the water. The pressure inside the bubble decays as it expands. The water is compressed, its pressure increases, which in turn, stretches the walls of the apparatus. Eventually, the pressure inside the bubble becomes equal to the pressure of the water, and the bubble ceases to expand.

EXAMPLE 1

Figure 2:
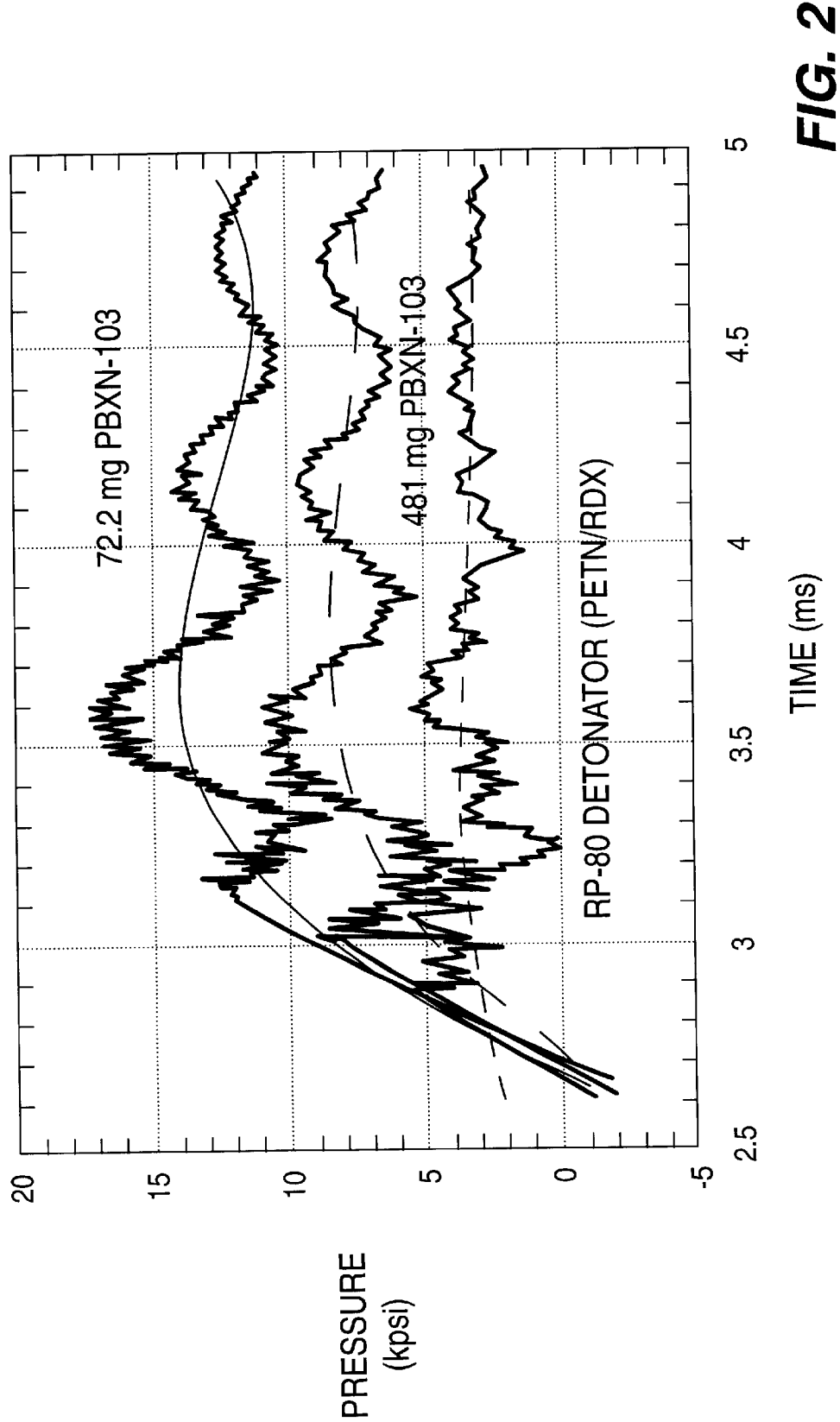

A steel apparatus having a chamber measuring approximately 1.5" in diameter and approximately 2" in height, with a rounded bottom of R equal to approximately ¾", and walls approximately 1" thick was used with approximately 10 shots. Small-scale tests were performed on an ideal PETN/RDX and two non-ideal ANFO and PBXN-103 explosives, as shown in FIG. 2. Experiments used the closed apparatus filled with water. The explosive was mounted in the chamber and a tourmaline gage was mounted in the head piece using a clear Silicone rubber compound, RTV615A (General Electric, Waterford Mass.) which was vacuum outgassed to remove trapped air from the compound prior to curing. The silicone rubber was in contact with the water inside the apparatus during the shot and transferred the pressure loading to the tourmaline gage which was potted inside it. RG-174 cable for the gage was epoxied into the head piece using M-bond Curing Agent, type 15 (Measurements Group, Inc., Raleigh N.C.). This prevented the water from leaking from the apparatus during high pressure loading. As seen in FIG. 2, the timing and rate of energy release of the non-ideal and ideal explosives is shown. This characterized the performance of the tested explosives.

The foregoing summary, description, examples and drawing of the invention are not intended to be limiting, but are only exemplary of the inventive features which are defined in the claims.

What is claimed is:

1. A reusable small-scale explosive testing apparatus, comprising:
    a structural member having a closed end and a receiving end forming a hollow cylindrical chamber therein, the chamber having a curved radius internal surface at the closed end and the chamber extending through the structural member at the receiving end, the chamber further having a substantially constant radius along the length of the structural member, the receiving end having an externally threaded circumference thereon;
    a head piece having an insertion component and covering component, wherein the insertion component fits into the chamber on the receiving end and partially fills the chamber; the covering component resting adjacent to the receiving end;
    a cap forming a cavity therein configured to receive the head piece, the cavity further forming internally threaded surface for mating with the externally threaded circumference of the structural member;
    a gage configured for units of pressure versus time measurements;
    a confinement liquid component of sufficient volume to fill the chamber for testing; and,
    means for releasing pressure extending from the structural member through the head piece and cap, wherein the means for releasing pressure is capable of retaining and releasing high pressures from the structural member.

2. The testing apparatus of claim 1, wherein the structural member comprises a high yield strength steel.

3. The explosive testing apparatus of claim 1, wherein the structural member comprises a length from about 3 inches to about 20 inches between the closed end and the receiving end.

4. The explosive testing apparatus of claim 1, wherein the structural member comprises a diameter of from about 3 inches to about 12 inches.

5. The explosive testing apparatus of claim 1, wherein the chamber comprises a length of from about 2 inches to about 20 inches.

6. The explosive testing apparatus of claim 1, wherein the chamber comprises a diameter of from about 1 inch to about 12 inches.

7. The explosive testing apparatus of claim 1, wherein the head piece comprises a composition comprising high yield strength steel.

8. The explosive testing apparatus of claim 1, wherein the cap comprises high yield strength steel.

9. The explosive testing apparatus of claim 1, further comprising a double o-ring seal having a first and second o-ring between the head piece and structural member.

10. The explosive testing apparatus of claim 1, wherein the space between the first and second o-ring comprising a distance of from about ½ inch to about 1 inch.

11. The explosive testing apparatus of claim 1, wherein the gage comprises a measuring device selected from the group consisting of transducer gage, tourmaline gage, ytterbium gage, carbon-resister gage, carbon foil gage and PVDF gage.

12. The explosive testing apparatus of claim 11, wherein the gage comprises the tourmaline gage.

13. The explosive testing apparatus of claim 11, further comprising a plurality of pressure-time gages.

14. The explosive testing apparatus of claim 1, wherein the means for releasing pressure comprises a capture container connected to the end of a pressure release hose.

15. A method for small-scale, explosive testing, comprising the steps of:
    providing a reusable small-scale explosive testing apparatus comprising a structural member having a closed end and a receiving end forming a hollow cylindrical chamber therein, the chamber having a curved radius internal surface at the closed end and the chamber extending through the structural member at the receiving end, the chamber further having a substantially constant radius along the length of the structural member, the receiving end having an externally threaded circumference thereon, a head piece having an insertion component and covering component, wherein the insertion component fits into the chamber on the receiving end and partially fills the chamber, the covering component resting adjacent to the receiving end, a cap forming a cavity therein configured to receive the head piece, the cavity further forming internally threaded surface for mating with the externally threaded circumference of the structural member, a gage configured for units of pressure versus time measurements, a confinement liquid component of sufficient volume to fill the chamber for testing and means for releasing pressure extending from the structural member through the head piece and cap, wherein the means for releasing pressure is capable of retaining and releasing high pressures from the structural member;
    inserting a sample amount of explosive into the chamber;
    filling the chamber with the confinement liquid;
    fitting the headpiece onto the receiving end of the structural member;
    screwing the cap onto the structural member;
    detonating the explosive sample;
    measuring the resulting high pressure of the detonated explosive sample; and,
    releasing the high pressure from within the chamber.

16. The method of claim 15, wherein the step of measuring the resulting high pressure comprises a pressure of from about 100,000 psig or less.

17. The method of claim 15, wherein the step of inserting a sample amount of explosive comprises a sample of from about 10 grams or less.

18. The method of claim 17, wherein the step of inserting a sample amount of explosive comprises a sample of from about 1 gram to about 100 milligrams.

19. A plurality of small-scale explosive tests comprising the method of claim 15, wherein a single reusable small-scale explosive testing apparatus is used.

20. A pressure evaluation product produced by the process comprising the steps of:
    providing a reusable small-scale explosive testing apparatus comprising a structural member having a closed end and a receiving end forming a hollow cylindrical chamber therein, the chamber having a curved radius internal surface at the closed end and the chamber extending through the structural member at the receiving end, the chamber further having a substantially constant radius along the length of the structural member, the receiving end having an externally threaded circumference thereon, a head piece having an insertion component and covering component, wherein the insertion component fits into the chamber on the receiving end and partially fills the chamber, the covering component resting adjacent to the receiving end, a cap forming a cavity therein configured to receive the head piece, the cavity further forming internally threaded surface for mating with the externally threaded circumference of the structural member, a gage configured for units of pressure versus time measurements, a confinement liquid component of sufficient volume to fill the chamber for testing and means for releasing pressure extending from the structural member through the head piece and cap, wherein the means for releasing pressure is capable of retaining and releasing high pressures from the structural member;

inserting a sample amount of explosive into the chamber;

filling the chamber with the confinement liquid;

fitting the headpiece onto the receiving end of the structural member;

screwing the cap onto the structural member;

detonating the explosive sample;

measuring the resulting high pressure of the detonated explosive sample; and, releasing the high pressure from within the chamber.

* * * * *